US00PP09446P

United States Patent [19]

van Andel

[11] Patent Number: Plant 9,446

[45] Date of Patent: Jan. 30, 1996

[54] ALSTROEMERIA VARIETY NAMED 'STABOPINK'

[75] Inventor: Jacob van Andel, Aalsmer, Netherlands

[73] Assignee: Van Staaveren B.V., Aalsmeer, Netherlands

[21] Appl. No.: 372,435

[22] Filed: Jan. 11, 1995

[51] Int. Cl.[6] ..... A01H 5/00

[52] U.S. Cl. ..... Plt./87.1

[58] Field of Search ..... Plt./87.1

*Primary Examiner*—James R. Feyrer

*Attorney, Agent, or Firm*—Christie, Parker & Hale

[57] ABSTRACT

A new and distinct Alstroemeria variety which is a spontaneous mutation of 'Stapink' and differs in having variegated foliage.

1 Drawing Sheet

BACKGROUND OF THE INVENTION

The present invention relates to a new and distinct variety of Alstroemeria discovered as a sport of the variety 'Stapink' among my collection of cultivated Alstroemeria maintained under controlled conditions in a greenhouse at Van Staaveren B.V., Aalsmeer, The Netherlands. The varietal denomation of the new variety is 'Stabopink'.

The first act of asexual reproduction of 'Stabopink' was in Aalsmeer, The Netherlands by propagation by dividing rootstocks. Asexual reproduction through successive generations has demonstrated that the combination of characteristics as herein disclosed for 'Stabopink' are firmly fixed and retained through successive generations of asexual reproduction.

'Stabopink' has not been observed under all possible environmental conditions. Phenotypic expression may vary with variations in environment such as temperature, light intensity, day length and growing and cultural conditions.

SUMMARY OF THE INVENTION

'Stabopink' is a spontaneous mutation of 'Stapink' and differs from the parent in the variegation of the leaves.

The plant produces numerous flowering stems, which is a desirable characteristics in a cut flower variety. The flower-bearing stems are of excellent quality. 'Stabopink' grows productively under greenhouse conditions and is also reproducible both by division of rhizomes and by tissue culture.

DESCRIPTION OF ILLUSTRATIONS

The new variety of Alstroemeria hybrid is illustrated in the accompanying illustration, which shows typical flower and variegated foliage characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by Color plate designations.

Botanical classification:

*Family.*—Amaryllidaceae.

*Genus.*—Alstroemeria sp.

*Commercial.*—Alstroemeria hybrid.

Origin: Spontaneous mutation of 'Stapink'.

PLANT

Form: Bush.

Shape: Upright.

Height: About 175 to 250 cm.

Internode length: About 1 to 4 cm.

Growth rate: Fast; the length of time (number of days) taken from young plants (i.e. rooted rootstocks, the stage of development in which the varieties are sold) to flowering stage under commercial greenhouse conditions is 80–90 days.

Pinching required: No.

Main stem or cane length: About 200 cm.

Growth: Vigorous.

Strength: Strong.

Foliage:

*Quantity.*—Abundant

*Number of leaves.*—About 30 to 40.

*Size of leaf.*—Length: About 10 to 17 cm. Width: About 2 to 3 cm.

*Shape of leaf.*—Elongated.

*Margin type.*—Straight.

*Texture.*—Glossy.

*Color.*—Upper side: Near 139A to 155D. Underside: Near 137C to 155D.

*Rhizomes.*—Yes.

Color: Near 155D. Size: About 10–30 cm.

INFLORESCENCE — FLOWER/FLORET

Blooming habit: Continuous.

Are spent umbels required to be pinched to maintain the claimed plant in a continuous blooming condition? — No.

Blooms: Profusely.

*Spring.*—Yes.

*Fall.*—Yes.

*Has tendency to give few blooms in fall.*—No.

Size: Medium.

*Diameter.*—About 5 cm.

*Depth.*—About 5 cm.

Stage when described: When first anthers release their pollen.

Borne: Singly in simple panicles.

Shape or form:

*When bloom first opens.*—Cup.

*When bloom matures.*—Cup.

Petalage:

*Numer of petals.*—6.

*Arrangement.*—2 concentric circles of 3 petals.

*Form.*—Obovate.

*Margin type.*—Minutely crimped; outer petals complete.

*Apex.*—Pointed.
*How long do petals stay on stem?—About* 2 weeks.
*Texture.*—Soft.
*Appearance.*—Velvety.
*Color (summer/fall).*—Outer petal/floret: Body near 55B; base near 37B; reverse side near 55B. Inner petal/floret: Base and apex of body near 32B and 55B respectively, with a central broad white band near 155D; the white band to the lateral inner petals having a central bright yellow spot near 12C, absent on the lower inner petal; the bottoms of these petals having similar color expressions. The two inner lateral petals have about 15–25 spots, color near 185A.

Peduncle or flower stem:
*Length.*—About 7 to 12 cm.
*Color.*—Near 137B to 137C.
*Strength.*—Strong.
*Upright.*—Yes.

Discoloration after full bloom? Slightly; main petal color, near 55B, turns to near 55C.
Is bloom affected by wet or hot weather? No.
Persistence (does flower hang on and dry?): No.
Disease resistance: Unknown.
Fragrance: None.
Lasting quality:
*On plant.*—About 3 weeks.
*As cut flower.*—About 12 to 14 days.

BUD

Size:
*Diameter.*—About 1–2 cm.
*Depth or length.*—About 2 to 3 cm.
Form or shape: Pear-shaped.
*Long.*—Yes.
*Pointed.*—No.
Rate of opening: Fast.

Color of petals/tepals:
*When petals first divide.*—Near 55D.
*When petals begin to unfurl.*—Near 55D.

Peduncle or flower stem:
*Length.*—About 7 to 12 cm.
*Hairy.*—No.
*Strength or character.*—Erect.
*Color.*—Near 137B to 137C.

REPRODUCTIVE ORGANS

Stamen:
*Number.*—6.
*Arrangement.*—Around the style.

Anthers:
*Size.*—About 8–10 mm.
*Color.*—Near 1B.

Filaments:
*Length.*—About 5 cm.
*Color.*—Near 55B.

Pollen:
*Color.*—Near 13B.

Pistils:
*Number.*—1.

Styles:
*Length.*—About 4–5 cm.
*Color.*—Near 54B.

Stigmas:
*Color.*—Near 55B.

FRUIT

Fertile: No.
Shape: Round.
Color at maturity: Near 163A.

I claim:

1. The new variety of Alstroemeria plant substantially as herein shown and described.

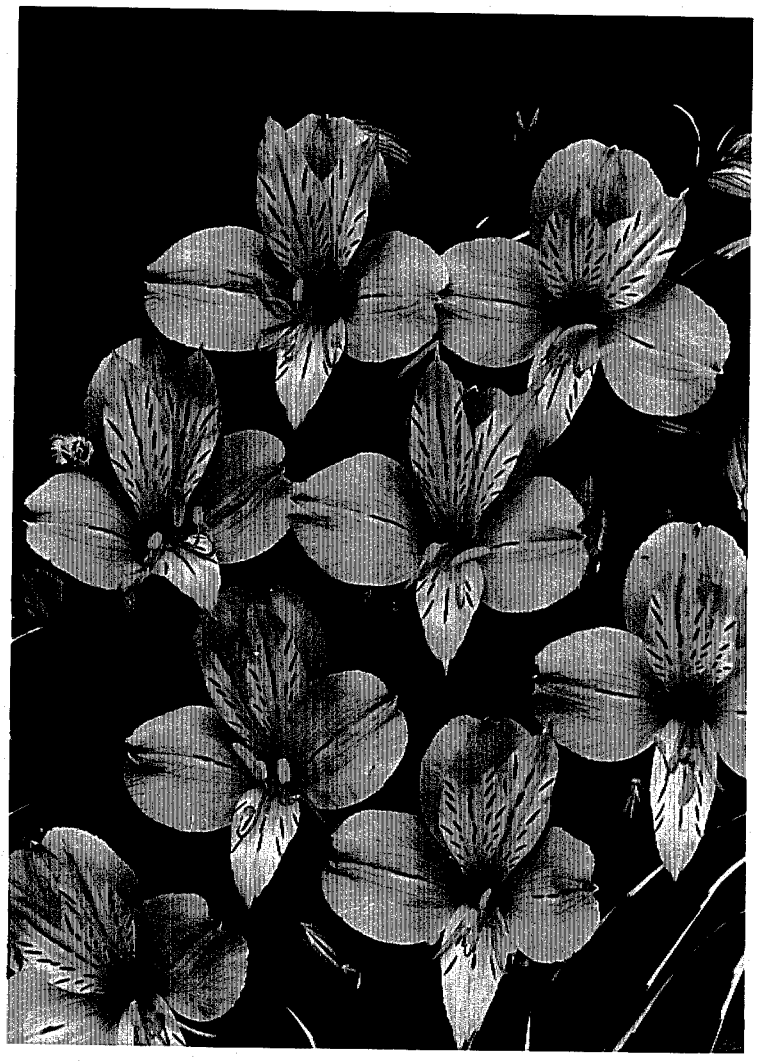

* * * * *